United States Patent [19]
Scott et al.

[11] Patent Number: 4,996,490
[45] Date of Patent: * Feb. 26, 1991

[54] MICROWAVE APPARATUS AND METHOD FOR MEASURING FLUID MIXTURES

[75] Inventors: Bentley N. Scott, Richardson; Y. Sam Yang, Plano, both of Tex.

[73] Assignee: Atlantic Richfield Company, Los Angeles, Calif.

[*] Notice: The portion of the term of this patent subsequent to Aug. 29, 2006 has been disclaimed.

[21] Appl. No.: 376,782

[22] Filed: Jul. 7, 1989

Related U.S. Application Data

[63] Continuation-in-part of Ser. No. 932,068, Nov. 18, 1986, Pat. No. 4,862,060.

[51] Int. Cl.$^5$ ...................... G01R 27/04; G01N 22/00
[52] U.S. Cl. .................................... 324/639; 324/460; 333/243
[58] Field of Search ............... 324/629, 637, 639, 640, 324/642, 643; 73/61 R, 61.1 R; 333/243; 174/102 C

[56] References Cited

U.S. PATENT DOCUMENTS

| | | | |
|---|---|---|---|
| 4,651,085 | 3/1987 | Sakurai et al. | 324/639 |
| 4,658,207 | 4/1987 | Scribano et al. | 324/664 |
| 4,764,718 | 8/1988 | Revus et al. | 324/637 |
| 4,774,680 | 9/1988 | Agar | 364/550 |
| 4,862,060 | 8/1989 | Scott et al. | 73/61 R |

*Primary Examiner*—Gerard R. Strecker
*Assistant Examiner*—Maura K. Regan
*Attorney, Agent, or Firm*—Michael E. Martin

[57] ABSTRACT

Apparatus for measuring the concentration of one material such as water in another material such as crude or refined oil including a coaxial microwave transmission line formed by a conduit for receiving the material and a center conductor which is sheathed with a dielectric covering which is operable to prevent short circuiting of the transmission path. An oscillator circuit is coupled to the transmission line and is driven by a free-running voltage controlled oscillator and a signal receiver monitors the change in frequency caused by impedance pulling of the oscillator due to the change in the dielectric constant of the mixture. Incident and reflected or transmitted power with respect to the measurement section is measured to determine whether an oil-in-water or water-in-oil emulsion is present to verify the concentration of one fluid in the other for a particular operating frequency.

17 Claims, 3 Drawing Sheets

MICROWAVE APPARATUS AND METHOD FOR MEASURING FLUID MIXTURES

CROSS REFERENCE TO RELATED APPLICATION

This application is a continuation-in-part of prior co-pending application Ser. No. 06/932,068 filed Nov. 18, 1986, now U.S. Pat. No. 4,862,060, and entitled "Microwave Apparatus for Measuring Fluid Mixtures". The prior application is hereby incorporated by reference in this application.

BACKGROUND OF THE INVENTION

1. Field of the Invention

The present invention pertains to a method and apparatus including an unbuffered oscillator for generating microwave frequency range radiation for measuring the composition of water-oil and other mixtures of matter and, in particular, wherein the mixture comprises a relatively high concentration of water in a water-oil mixture.

2. Background

The above-referenced patent application describes a microwave-based apparatus for measuring the concentration of one liquid in another, particularly relatively low concentrations of water in oil. In the production and transportation of crude oil, for example, it is important to be able to determine the amount of water mixed with the crude oil, which is often present as naturally-produced water or water which has become mixed with the oil as a result of certain reservoir stimulation processes. In some instances relatively high percentages of water in oil occur as a result of producing from formations which have a so-called "high water cut". In many crude oil reservoirs, the percentage of water in the produced liquid mixture may easily exceed 50% and go as high as 80% or 90%, at least at various times in the production process.

The apparatus described in application Ser. No. 06/932,868 provides an unbuffered or unisolated, free-running oscillator circuit which is connected to a fluid measurement section having a coaxial transmission path comprising a conduit having a center conductor extending through the conduit and wherein the conduit itself forms a part of the conductive path or circuit. The apparatus is capable of detecting a change in operating frequency of the oscillator as a function of the change of the composition of the liquid mixture being conducted through the conduit of the measurement section. In particular, the apparatus is utilized to determine the change in percentage of water contained in the oil flow-stream and at relatively low percentages (less than 5% to 10%) of water in oil, wherein the water exists as dispersed droplets, a water-in-oil emulsion.

For relatively low percentages of water in oil the change in the oscillator circuit operating frequency can be easily measured and compared to an pre-established relationship between oscillator operating frequency and the composition of the water-in-oil mixture to determine the water content. However, when the water content of the composition increases to about 50% to 86%, by volume, the mixture becomes inverted to an oil-in-water emulsion and apparatus with a metal center conductor and a metal outer conductor/conduit in direct contact with the mixture being measured undergoes a loss in field intensity due to a short circuit between the conductor elements. This occurrence renders the aforementioned apparatus essentially incapable of measuring the water content of the composition.

However, in accordance with the present invention an apparatus which includes a center conductor as described herein and the practice of the improved method of determining the composition of a material, which includes measuring power loss of microwave radiation being propagated through the apparatus, can be used to determine the water content of a liquid mixture or composition having a relatively high percentage of water, including an oil-in-water emulsion.

SUMMARY OF THE INVENTION

The present invention provides an improved apparatus for utilizing microwave energy, the frequency of which varies when transmitted through a transmission line with the concentration of at least one medium in a composition of material which is present as a dielectric material in the transmission line. In particular, the present invention includes an apparatus with an improved coaxial transmission line wherein a fluid medium is flowing through a conduit forming an outer conductor in which is disposed a center conductor having a covering of a material with suitable dielectric properties to enable the measurement of relatively high concentrations of one liquid in another.

Further in accordance with the present invention, there is provided an apparatus which includes a relatively high frequency unbuffered, free-running oscillator which generates radio frequency range or so-called microwave range energy which is transmitted through an RF transmission line which also receives a flow-stream of fluid. The net complex impedance of the transmission line varies with the concentration of one fluid in another to change the operating frequency of the oscillator, which frequency is measured and compared with a known frequency range to determine the concentration of the one fluid from reference data. In particular, the transmission line includes a center conductor with an outer sheath or layer which is formed of a material having dielectric characteristics which are such as to prevent a short circuiting of the conductive path between the center conductor and the outer conductor at an unwanted location in the transmission line. The sheath is preferably formed of a non-metallic material having a low loss tangent dielectric characteristic. Such material includes polypropylene, fluorocarbon plastics, and ceramic materials. At least in the instance of use of a polypropylene material or a material made under the trademark Delrin, the ratio of the diameter of the outer sheath or sleeve to the diameter of the center conductor of metal is preferably approximately two to one.

Still further in accordance with the present invention, there is provided a method and apparatus for measuring the composition of a material, such as the water content of a water-oil mixture, wherein the characteristics of the mixture when changing from a water-in-oil emulsion to an oil-in-water emulsion can be detected to eliminate false readings of the concentration of one of the liquids in the other. In particular, the present invention provides an improved method for determining reliably whether a water-in-oil or oil-in-water mixture is present by comparing, at a particular oscillator operating frequency, the microwave power loss incurred by the apparatus. The present invention also provides a microwave transmission based apparatus for measuring the concentration of one liquid in another, such as a water-in-oil or oil-in-water which includes directional couplers arranged in such a way as to measure the incident microwave power on the measurement section of the apparatus and the reflected microwave power so that a power loss determination can be made.

The above-mentioned features and advantages of the present invention together with other superior aspects thereof will be further appreciated by those skilled in the art upon reading the detailed description which follows in conjunction with the drawing.

DESCRIPTION OF PREFERRED EMBODIMENTS

Figure 1:
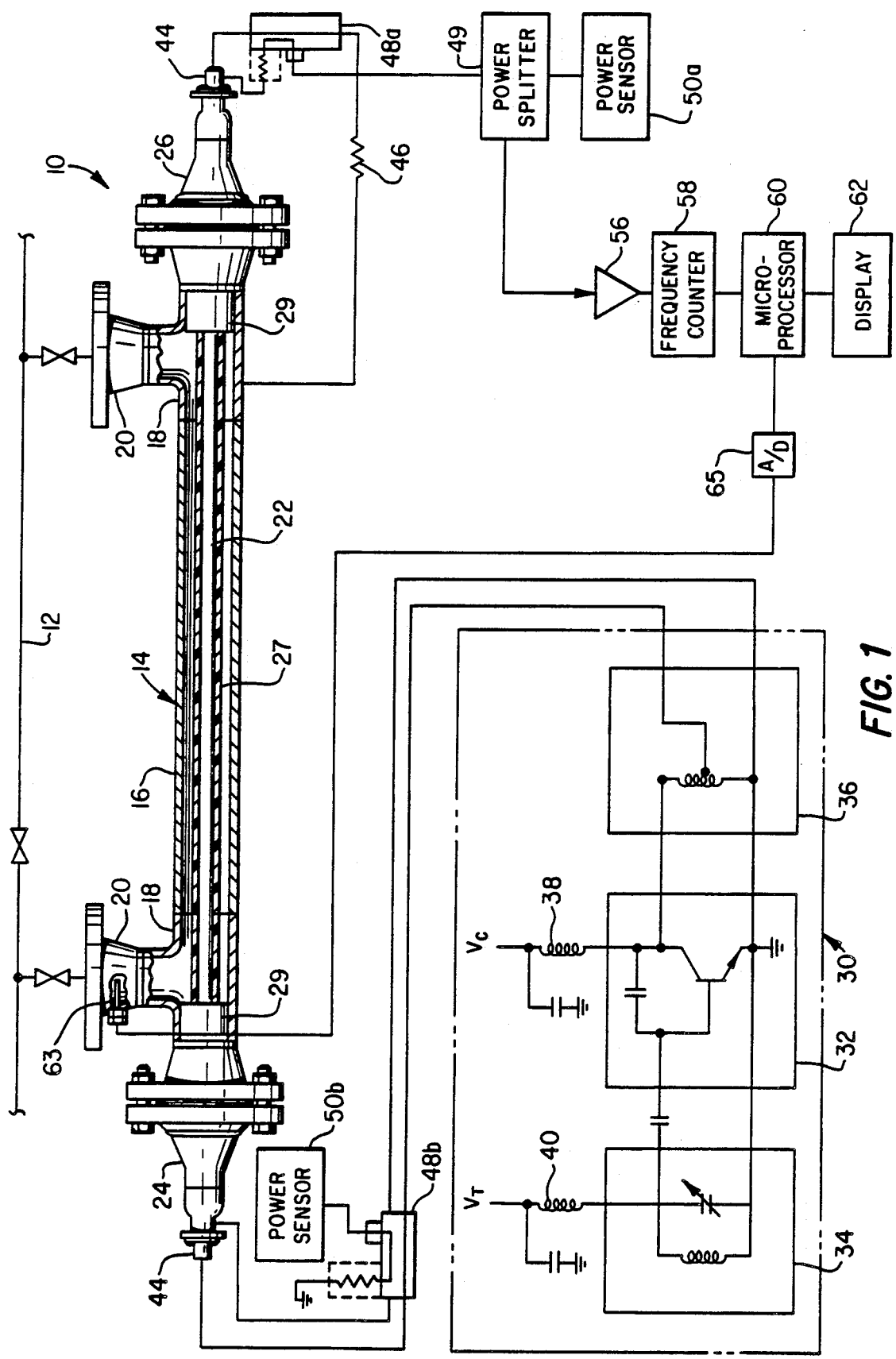
FIG. 1 is a schematic diagram of one preferred embodiment of the apparatus of the present invention.

In the description which follows, like parts are marked throughout the specification and drawing with the same reference numerals, respectively. The drawing figures are in generally schematic form and certain conventional or commercially available elements are shown in block diagram form only in the interest of clarity and conciseness.

Referring to FIG. 1, there is illustrated a diagram of an apparatus for measuring the concentration of one substance or material such as water, in another substance or material such as crude oil, which is being transmitted as a liquid mixture flowstream through a pipeline. The apparatus is generally designated by the numeral 10 and is particularly adapted for interconnection with a fluid transmission pipeline 12 for sampling the pipeline flowstream. Alternatively, the apparatus 10 might become part of the pipeline. The apparatus 10 includes a fluid flow conducting and measurement section 14 comprising an outer conduit section 16, including spaced apart pipe tee sections 18 having conventional flange portions 20 formed thereon for connection to branch conduit portions of the pipeline 12. The measurement 14 comprises a coaxial transmission line which includes a center conductor 22 preferably formed of a metal such as stainless steel which extends between opposed end support parts 24 and 26 which are described in detail in the above-referenced patent application. The center conductor 22 preferably comprises a generally cylindrical rod or tube member coaxially arranged in the conduit 16 and provided with an outer sheath 27 formed of a material having a relatively low dielectric loss tangent, preferably less than 0.1 at a frequency of 1.0 GHz. The sheath 27 preferably comprises a relatively easy-to-fabricate plastic such as polypropylene, a plastic sold under the trademark Delrin or one of the fluorocarbon plastics. Alternatively, certain ceramics or other materials may also be used as the outer sheath 27 as long as they are low loss tangent dielectric materials. The fit between the outer sheath 27 and the center conductor 22 is preferably a forced or line-to-line fit although some clearance may be permitted as long as fluid flow between the center conductor and the outer sheath is prohibited. In an apparatus where the center conductor has a diameter of 0.25 inches, the outer diameter of the sheath 27 is preferably at least about 0.50 inches or, alternatively, a ratio of the outer diameter of the sheath to the outer diameter of the center conductor is in the range of about two to one.

It has been determined that with the provision of a sheath 27 formed of one of the above-mentioned materials and in the proportions described, that the electrical circuit for propagating microwave radiation through the apparatus 22 retains a high quality signal resolution characteristic in liquid mixtures of oil and water, for example, wherein the water content is relatively high, that ia on the order of more than 5% to 10% by volume. With this type of center conductor arrangement, the circuit associated with the apparatus 10 and described hereinbelow retains good field intensity or prevents short circuiting of the center conductor to the outer conductor in an unwanted location, the oscillator circuit retains its good load-pulling characteristics with good resolution of phase and the interface between the sheath 27 and the fluid in the conduit 16 is a new propagation medium which has desirable operating characteristics.

When the apparatus 10 is operating with a liquid composition which is high in water content or a so-called water continuous phase, the conductivity of the composition is high compared to a good dielectric but low compared to a good conductor and, of course, the liquid composition is in direct contact with the wall surfaces of the measurement section 14 including the center conductor. The insulating sheath 27 prevents the radio frequency (RF) energy from being shorted out immediately at the point where the RF energy enters the measurement section or where the fluid cross section begins. Moreover, the sheath 27 now becomes the primary region where the RF field is propagated with the conductive fluid becoming a pseudo outer wall of the measurement section in place of the wall of the conduit 16. The cross sectional measurement of the water-in-oil composition is still preserved due to the large skin depth of the microwave or RF energy at the operating frequency. This skin depth is large through the water as the conducting medium of the outer half of the coaxial transmission line formed by the measurement section. The dielectric structure is now the sheath 27. The properties of the propagated RF energy still reflect the changing content of the oil in the water and this is related through pulling of the unisolated oscillator which is described hereinbelow. The sheath 27 must be thick enough to maintain a reasonable coaxial impedance to be able to propagate the RF energy into the measurement section 14 and maintain a measurement capability. A very thin dielectric coating on the center conductor 22 will cause a very low impedance with a liquid composition having a high water content and therefore the RF energy would be reflected at the fluid interface.

RF energy is not propagated in the interior of a good conductor. The conductor guides the electromagnetic waves. The energy travels in the region between the conductors in a coaxial transmission system with a good dielectric. The currents that are established at the conductor surfaces propagate into the conductor in a direction perpendicular to the direction of the current density. The current density or electric field intensity established at the surface of a good conductor decays rapidly looking into the conductor. When the conductor is resistive or, low conductivity, this depth into the conductor increases rapidly. This phenomenon is known in the art as skin depth.

As shown in FIG. 1, the center conductor 22 extends through opposed end block members 29 which are also preferably formed of a relatively high insulative material such as a fluorocarbon plastic and the end plug sections are configured in a way similar to the ones described in the above-referenced patent application.

The measurement section 14 is operably connected to a source of radio frequency (RF) or so-called microwave energy comprising an unbuffered or unisolated, free-running oscillator, generally designated by the numeral 30. The oscillator 30 includes an active circuit 32 operably connected to a tuning circuit 34 and to an impedance matching network circuit 36. The circuit 32 is adapted to receive a constant DC voltage, $V_c$, from a source not shown and by way of a filter circuit 38. The tuning circuit 34 is also adapted to receive a controllable DC voltage, $V_t$, from another source, not shown, by way of a second filter circuit 40. The oscillator 30 has an appreciable load-pulling characteristic. The fundamental operating frequency of the oscillator is changed as the complex load is changed on the output circuit of the oscillator. The oscillator 30 is preferably of a type commercially available such as from Avantek Company, Santa Clara, Calif. as their model VTO 8030 voltage controlled oscillator. The exemplary oscillator 30 has a maximum load-pulling characteristic of about 35 MHz at a nominal 200 MHz operating frequency into all phases of a short circuit at the end of a 50 Ohm line stretcher (approximately 0.5 DB return loss). The oscillator 30 is operably connected to the apparatus measurement section 14 through a suitable connector 44 which is in electrically conductive engagement with the center conductor 22 at the end part 24 and at the opposite end of the center conductor 22 through a second connector 44, a resistance 46 and with the outer conductor or conduit 16 as illustrated. The end part 26 is also adapted to connect the center conductor 22 with a 10 DB directional coupler 48a which is operable to sample the microwave energy or power transmitted through the coaxial measurement section 14. The coupler 48a is connected to a power splitter 49 which is connected to a power sensor 50a. The directional coupler 48a may be of a type manufactured by Minicircuits Company of Brooklyn, N.Y. as their model ZED-15-2B. The power splitter 49 may be of a type ZFSC-2-2 also manufactured by Minicircuits. The power sensor 50 may be of a type 437B manufactured by Hewlett Packard of Sunnyvale, Calif.

A second directional coupler 48b is interposed in the circuit between the end part 24 and the oscillator 30 and is connected to a second power sensor 50b. The directional couplers 48a and 48b may be of identical configuration. The coupler 48a is connected to the power splitter 49 which provides an output signal which is amplified by an amplifier 56. The output of the amplifier 56 is adapted to be input to a frequency counter 58 which is also adapted to be connected to a microprocessor 60. A suitable digital display or readout device 62 is connected to the microprocessor 60. The amplifier 56 may be of a type commercially available from the above-mentioned Minicircuits Company as their model ZFL-500. The frequency counter 58 may be of a type manufactured by Hewlett Packard Company as their model 5342A and the microprocessor 60 may be a Hewlett Packard type 9836. The system illustrated in FIG. 1 preferably includes a temperature compensation circuit including a thermocouple 63 operably connected to a conversion circuit 65 to provide a suitable digital signal to the microprocessor 60.

In operation, the changing dielectric constant presented by the material flowing through the measurement section 14, such as caused by the presence in a liquid mixture, for example, of varying amounts of water in oil or oil in water, causes the oscillator 30 to change its operating frequency over a relatively narrow frequency band as compared with the nominal operating frequency of the oscillator. For example, the oscillator 30, in a preferred form, can be pulled from its nominal operating frequency through a range of about 20 MHz by the changing dielectric constant of the medium flowing through the measurement section 14.

Figure 2:
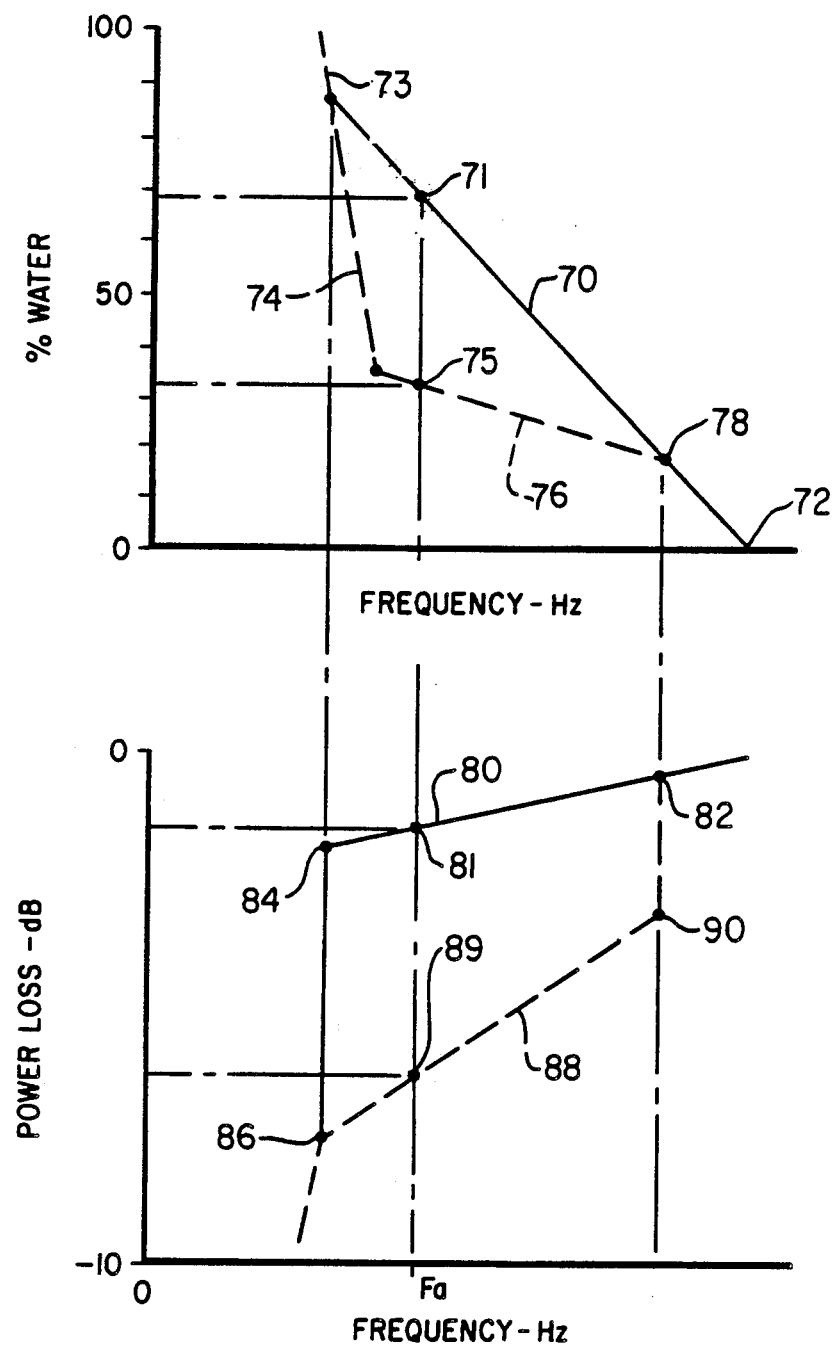
FIG. 2 is a diagram illustrating the change in frequency of the oscillator circuit of the apparatus as a result of the change in concentration of one substance such as water in another substance such as oil and including a diagram showing the change in microwave power loss with the change in the concentrations.

Referring to FIG. 2, the two diagrams illustrated indicate the characteristics of the change in oscillator operating frequency as a function of the concentration of water in an oil such as crude petroleum. The graphical representations of FIG. 2 are meant to be of a somewhat general nature and the abscissas of both graphs are not indicated to have any particular numerical values. However, the frequency of operation of the oscillator 30 as a function of the percentage of water in a water-oil mixture is indicated by the curve or line 70. For example, at a percentage of water approximately nil or zero, the operating frequency of the oscillator 30 would be indicated by the point 72 and, from experiments, as the percentage of water in a water-crude petroleum mixture increases to about 50% of the total volume, the water exists as an emulsion in an oil liquid. In a range of concentration of about 50% to 86% water an inversion may occur wherein the emulsion becomes one of oil-in-water rather than water-in-oil. Above 86% water, almost universally, the emulsion is one of oil in water. A slight increase in the slope of the curve 70 occurs over the portion 73 in the range of 86% to 100% water in the liquid mixture being measured. It has been observed that when increasing the concentration of water in a water-oil mixture, the characteristic of the frequency change is indicated by the curve 70. However, in instances where a relatively high concentration of water in the mixture is initially present but then decreases, and/or wherein an oil-in-water emulsion exists, the change in oscillator operating frequency follows a curve 74 as indicated by the dashed line in the frequency versus percentage of water diagram. This dashed line follows the slope indicated in the diagram to a point wherein the amount of water equals about 36% by volume of the mixture wherein the slope of the curve changes to follow the line 76 to the point where it intersects the curve 70 as indicated at 78. Accordingly, it has been observed that with changing conditions of a liquid mixture comprising water and oil, for example, that a measurement of frequency alone as an indication of the percentage water in the mixture may be unreliable since, in the range of about 20% to 86% water in the mixture by volume, more than one frequency can be indicated by the apparatus 14.

However, it has been discovered in accordance with the present invention that there is also a change in the microwave radiation power loss through the measurement section 14 as a function of the condition wherein there is either a water-in-oil mixture or an oil-in-water mixture. Looking at the diagram which represents frequency in the abscissa versus microwave power loss in the ordinate, the solid line curve 80 indicates the power loss through the measurement section 14 for a condition of water-in-oil from the point 82 to the point 84, 86. The dashed line 88 in the diagram of frequency versus power loss indicates the power loss for a condition wherein the mixture is essentially an oil-in-water emulsion.

Accordingly, during operation of the system 10 the incident power sensed at the power sensor 50b as input to the measurement section 14 may be monitored and the transmitted power as determined by the power sensor 50a may also be monitored. The difference between the readings of these power sensors is then measured to determine the power loss at a particular operating frequency of the oscillator circuit 30. By determining the microwave radiation power loss, a characteristic of the material being analyzed may be noted, such as, in a water-oil mixture, the condition wherein a water-in-oil or oil-in-water emulsion is present. For example, at an operating frequency of $F_a$ if the power loss corresponds to the loss indicated by the curve 88 at point 89, it is indicated that an oil-in-water mixture exists. Accordingly, for the same frequency, viewing the diagram of frequency $F_a$ versus percentage water, it is indicated that approximately 30% water is present. On the other hand, for an operating frequency $F_a$, if the power loss corresponds to that indicated by the curve 80 at point 81, it is known that a much higher percentage of water is present in a so-called water-in-oil mixture and corresponding to the percentage of water indicated by the point 71 on line 70, for operating frequency $F_a$.

Figure 3:
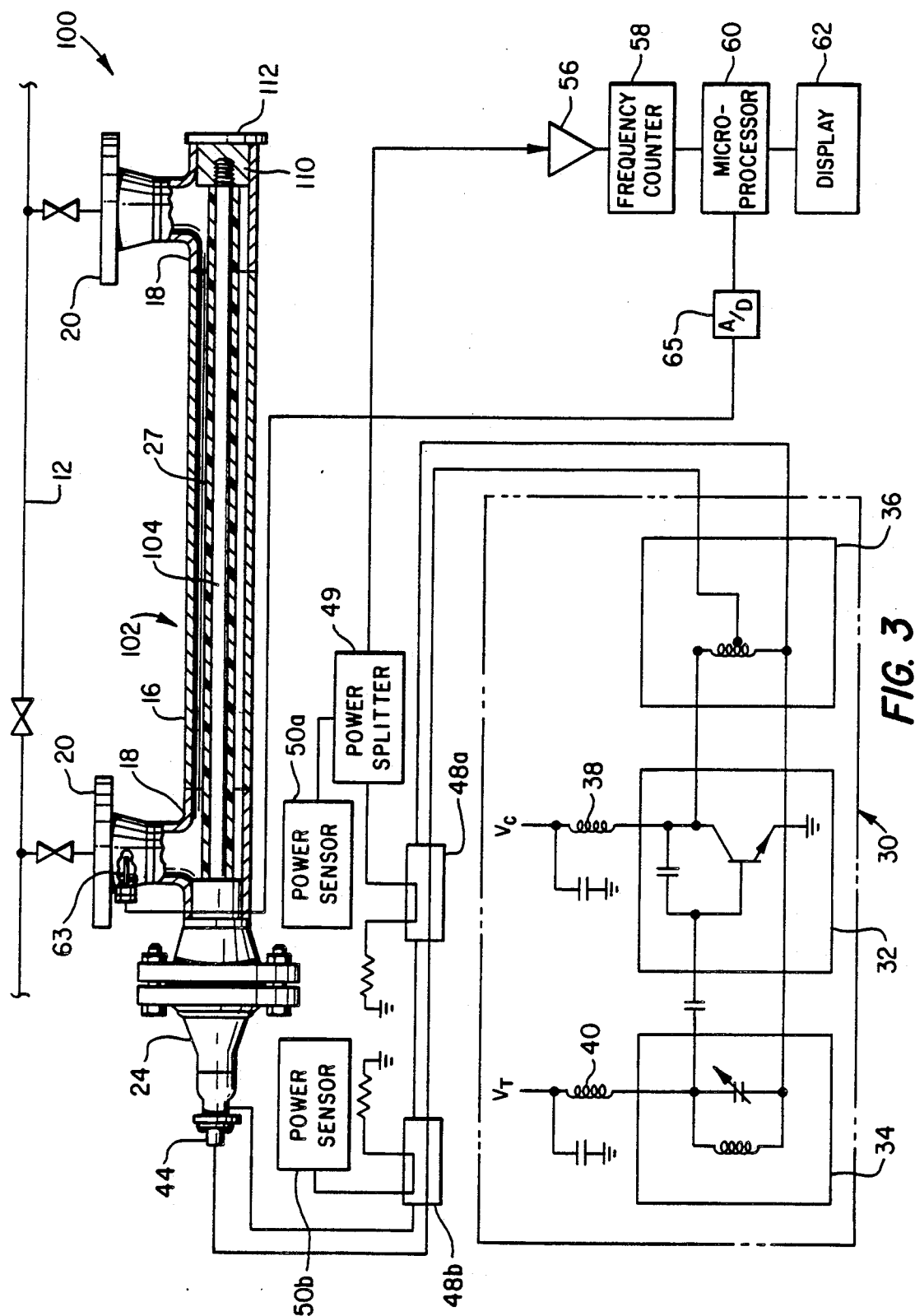
FIG. 3 is a schematic diagram of an alternate embodiment of the apparatus of the present invention.

Referring now to FIG. 3, there is illustrated an alternate embodiment of a measurement apparatus in accordance with the present invention and generally designated by the numeral 100. The apparatus 100 also includes a measurement section 102 formed by an outer conductor and conduit 16, a center conductor 104 and an outer sheath 27 for the center conductor. The apparatus 100 includes an end part 24 connected to the conduit 16 together with the conduit tee sections 18 and flanges 20 as provided for the apparatus measurement section 14.

The apparatus 100 differs from the apparatus 10 primarily in regard to the end of the measurement section opposite the end part 24. As illustrated, the center conductor 104 terminates in a plug member 110 having an integral flange portion 112 which is suitably secured to the tee section 18 such as by welding or other conventional means. The end plug 110 is of a highly conductive type material to form a short circuit between the center conductor 104 and the conduit 16.

The oscillator circuit 30 is suitably connected to directional couplers 48a and 48b which are arranged to measure the incident power transmitted to the measurement section 102 and the reflected power returned from the measurement section 102. A power splitter 49 is connected in circuit with the coupler 48a and a power sensor 50a is adapted to measure the incident power transmitted to the measurement section 102. In like manner, a power sensor 50b is operably coupled to the directional coupler 48b to measure the reflected power. The change in operating frequency of the oscillator circuit 30 is sensed by the circuit which includes the amplifier 56, frequency counter 58, microprocessor 60 and display device 62.

The operation of the apparatus 10 and the apparatus 100 are essentially the same. By sweeping the oscillator operating frequency of the circuit 30 across a frequency range suitable for the particular material being measured, including the maximum range of component composition, a change in the operating frequency for a particular tuned frequency may be compared with the output of the oscillator 54 and a differential, relatively low frequency signal may be output from the mixer 52 to the frequency counter 58. The frequency counted by the counter 58 may be compared with frequency data stored in the microprocessor 60 and corresponding to a range of percentages of one medium in another such as water in oil and oil in water. Concomitant with the change in operating frequency the power loss characteristic of the measurement sections 14 and 102 may be measured by comparing the power at the power sensors 50a and 50b for a particular operating frequency and by referring to the diagram of frequency versus mixture content and frequency versus power loss to determine whether, in the case of a water-oil mixture, a water-in-oil condition exists or an oil-in-water condition exists and wherein the percentage of one in the other may be determined. The diagrams of FIG. 2 may, of course, be presented in a digital data base accessible by a suitable computer.

Although preferred embodiments of the present invention have been described in detail herein, those skilled in the art will recognize that various substitutions and modifications may be made to the method and apparatus described without departing from the scope an spirit of the invention as recited in the appended claims.

What is claimed is:

1. Apparatus for measuring the concentration of one fluid such as water in a fluid mixture which includes another fluid such as oil using the alteration of microwave energy characteristics, said apparatus comprising:
   means forming a measurement section including
      means forming a coaxial microwave transmission line including an outer conductor comprising a conduit for said fluid mixture and a center conductor extending within said conduit;
   means forming a sheath around said center conductor and having a low dielectric loss tangent so as to minimize the termination of an electrical field being propagated through the transmission line due to the conductivity of said fluid mixture; and
   an oscillator circuit operably connected to said transmission line for generating microwave energy for propagation through said measurement section at an operating frequency which changes with a change in the complex impedance of the oscillator load which includes the properties of said fluid mixture in said measurement section.

2. The apparatus set forth in claim 1 including:
   means for measuring a change in the operating frequency of said oscillator circuit resulting from the properties of the fluid mixture in said measurement section; and
   means for comparing the change in frequency with a reference frequency corresponding to a certain concentration of one fluid in the other.

3. The apparatus set forth in claim 1 wherein:
   said means forming said sheath comprises a material selected from one of polypropylene plastic, a fluorocarbon plastic and a ceramic.

4. The apparatus set forth in claim 1 or 3 wherein:
   said means forming said sheath has a dielectric loss tangent of less than about 0.1 at 1.0 GHz.

5. The apparatus set forth in claim 3 wherein:

said center conductor and said sheath are cylindrical and the diameter of said sheath is about twice the diameter of said center conductor.

6. The apparatus set forth in claim 1 wherein:
said oscillator circuit includes an unisolated oscillator operably connected to said measurement section.

7. The apparatus set forth in claim 6 wherein:
said oscillator is a free-running voltage controlled oscillator.

8. The apparatus set forth in claim 1 including:
means for measuring the microwave radiation power loss in said measurement section.

9. The apparatus set forth in claim 8 wherein:
said means for measuring the microwave radiation power loss includes a first directional coupler interposed between said oscillator circuit and said measurement section and a power sensor operably connected to said first directional coupler; and
a second directional coupler interposed between said measurement section and means for measuring the operating frequency of said oscillator circuit commensurate with a change in the concentration of one fluid in the fluid mixture and a power sensor operably connected to said directional coupler for measuring the power transmitted through said measurement section.

10. The apparatus set forth in claim 1 wherein:
said center conductor is in electrically conductive engagement with said conduit at one end of said measurement section.

11. The apparatus set forth in claim 10 including:
means for determining the power loss of microwave radiation in said measurement section.

12. The apparatus set forth in claim 11 wherein:
said means for determining power loss includes first and second directional couplers in circuit with said oscillator circuit and said measurement section, respectively.

13. The apparatus set forth in claim 12 including:
means operably connected to said first directional coupler for measuring the operating frequency of said oscillator circuit.

14. The apparatus set forth in claim 13 including:
power sensor means operably connected to said first directional coupler for measuring the incident power imposed on said measurement section by said oscillator circuit.

15. The apparatus set forth in claim 12 including:
power sensor means operably connected to said second directional coupler for measuring the reflected power of microwave radiation transmitted from said measurement section.

16. A method for measuring a property of a composition of matter using the alteration of microwave radiation characteristics comprising the steps of:
providing apparatus including means forming a measurement section having means for transmitting microwave radiation therethrough;
providing an oscillator circuit operably connected to said means for transmitting microwave radiation at an operating frequency which changes with a change in the complex impedance of the oscillator load which includes the properties of the composition of matter in said measurement section;
providing means for measuring a change in said operating frequency;
providing means for measuring the incident power to said measurement section and the transmitted power through said measurement section to determine the power loss of microwave radiation in said measurement section;
energizing said oscillator circuit and measuring changes in the operating frequency of said oscillator circuit due to changes in the composition of matter in said measurement section;
determining the power loss of microwave radiation in said measurement section at a selected operating frequency; and
comparing the power loss at said operating frequency with a reference power loss for a known condition of said composition of matter for determining said property.

17. The method set forth in claim 16 wherein:
said composition of matter includes water-oil mixture and said step of measuring the power loss includes comparing the power loss to a reference power loss exhibited by a water-in-oil emulsion and a reference power loss of an oil-in-water emulsion at a particular operating frequency to determine the concentration of at least one of said water and oil in said mixture.

* * * * *